US005736518A

United States Patent [19]
Politi et al.

[11] Patent Number: 5,736,518
[45] Date of Patent: Apr. 7, 1998

[54] PEPTIDE COMPOUNDS OF (L) AMINO ACIDS AND RING MOLECULES, AND THERAPEUTICAL APPLICATIONS THEREOF

[75] Inventors: Vincenzo Politi; Giovanni Di Stazio; Andrea Margonelli; Giovanna De Luca, all of Rome, Italy

[73] Assignee: Polifarma S.p.A., Rome, Italy

[21] Appl. No.: 573,399

[22] Filed: Dec. 15, 1995

Related U.S. Application Data

[63] Continuation of Ser. No. 311,449, Sep. 26, 1994, Pat. No. 5,504,071, which is a continuation of Ser. No. 867,231, filed as PCT/IT91/00080 on Oct. 3, 1991, abandoned.

[30] Foreign Application Priority Data

Oct. 3, 1990 [IT] Italy ................. 48335/90

[51] Int. Cl.[6] ................... A61K 38/00; A61K 38/06
[52] U.S. Cl. ................... 514/18; 530/331; 530/800
[58] Field of Search ................. 514/18; 530/331, 530/800

[56] References Cited

U.S. PATENT DOCUMENTS

| | | | |
|---|---|---|---|
| 4,216,209 | 8/1980 | Bellini et al. | 514/18 |
| 4,456,594 | 6/1984 | Pfeiffer | 514/18 |
| 5,051,404 | 9/1991 | Sisto et al. | 514/18 |
| 5,115,098 | 5/1992 | Burakoff et al. | 514/18 |

FOREIGN PATENT DOCUMENTS

| | | |
|---|---|---|
| 518836 | 4/1978 | Australia . |
| 148133 | 12/1984 | European Pat. Off. . |
| 204374 | 5/1986 | European Pat. Off. . |
| 2585709 | 2/1987 | France . |

OTHER PUBLICATIONS

Greenlee (1987) *Pharm. Res.*, 4(5), 364–374.
Bolis et al. (1987) *J. Med. Chem.*, 30(10), 1729–1737.
Plattner et al. (1988); *J. Med. Chem.*, 31(12), 2277–2288.
Haber et al. (1987) *J. Cardiovas. Pharm.*, 10, 554–558.
Burger (1960) "Medicinal Chemistry", 2nd Ed. Interscience Publisheres, New York, pp. 565–581, 600–601.
Aldrich Catalog (1990–1991), pp. 112, 1064, 1234.

*Primary Examiner*—John P. Weber
*Attorney, Agent, or Firm*—Birch, Stewart, Kolasch & Birch, LLP

[57] ABSTRACT

Compounds of general formula A—B—C in which: A is a monovalent radical of a L-ring molecule; B is a bivalent radical of a L-α-aminoacid; and C is a monovalent radical of a L-aromatic molecule. The compounds show an antihypertensive, analgesic, immuno-modulating and antiinflammatory activity, they are resistant to enzyme hydrolysis and they can be used for the preparation of drugs for oral administration.

22 Claims, No Drawings

PEPTIDE COMPOUNDS OF (L) AMINO ACIDS AND RING MOLECULES, AND THERAPEUTICAL APPLICATIONS THEREOF

This application is a continuation of application Ser. No. 08/311,449, filed on Sep. 26, 1994, now U.S. Pat. No. 5,504,071, which is a continuation of application Ser. No. 07/867,231, filed Jun. 2, 1992, now abandoned, the entire contents of which are hereby incorporated by reference.

TECHNICAL FIELD

The present invention has as its object compounds having multiple pharmacological activity, and having present in their molecule a sequence of three radicals, of which the central one is an α-amino acidic radical. These compounds, which show a good level of resistance to enzymatic hydrolysis, can be used in the preparation of drugs, in particular for oral use, having anti-hypertensive, analgesic, immunomodulating and antiinflammatory activities.

1. Background Art

As is known, in Italian patents No. 1 172 391 and 1 186 733, and in the published Italian patent application No. 48430A89, molecules of peptidic nature are known, having anti-hypertensive, analgesic and immunomodulating activity, characterized by the sequence of three radicals of specific α-amino acids.

Said compounds have been shown to work well in the preparation of drugs having the above characteristics.

However, their use has been limited to administration by injection, due to the low resistance shown by these compounds to enzymatic hydrolysis.

2. Disclosure of the Invention

It has now been surprisingly found that the use of compounds according to the present invention makes it possible to overcome the above-mentioned limitation, while at the same time offering other advantages which will be clearly seen from the following. Object of the present invention are compounds of general formula

A—B—C in which

A is a monovalent radical of a (L)-ring molecule selected from the group comprising:

in which
X can be $CH_2$, S or CHOH
n can be 0, 1, 2
$R^1$ can be H or $CH_3$
R can be H, $CH_3$, or a generic nitrogen blocking group as used in the synthesis of peptides, such as CBZ, BOC, Fmoc and acetyl
Y can be $CH_2$ or CO
Z can be NH, $NCH_3$, O or S;
B is the bivalent radical of a neutral (L)-α-amino acid, selected from the group comprising glycine, leucine, alanine or valine; and
C is the monovalent radical of a (L)-aromatic amino acid, selected from the group comprising tryptophan, phenylalanine, phenylglycine, and salts, esters and amides thereof, or one of the compounds listed below, and salts, esters and amides thereof, in which
$R^1$ has the meaning previously indicated, and
$R^2$ can be H, OH, $OCH_3$ or $CH_3$,
with the proviso that when A is in which
R has the meaning previously indicated, with the exclusion of $CH_3$,
then C cannot be either a residue of tryptophan, or of phenylalanine.

The present invention also extends to drugs with antihypertensive, analgesic, immuno-modulating and antiinflammatory activity, characterized by the fact that they contain at least one of the compounds represented by the above general formula.

These drugs can be taken orally.

The present invention also extends to the use of compounds of the general formula indicated above for the preparation of drugs, for example for oral use, for the treatment of states of hypertension, for pain therapy, for the modulation of immune responses and for the treatment of inflammatory states.

The drugs according to the present invention can naturally contain non-toxic, pharmaceutically inert, support materials. Among the suitable non-toxic, pharmaceutically inert support materials can be included solid, semi-solid or liquid diluents, various fillers and additives, for example binding, moistening, reticulating and adsorbtion agents, agents for delaying solution and accellerating absorption.

Examples of the possible pharmaceutical preparations can include tablets, sugar-coated pills, capsules, pills, granulates, suppositories, solutions, suspensions and emulsions, pastes, ointments, gels, cremes, lotions, powders and sprays.

Tablets, sugar-coated pills, capsules, pills and granulates can be provided with the usual coatings and coverings, if necessary containing opacifiers, and they can be compounded in such a way as to release the active agents only or preferably in a certain part of the intestine, with delayed action if necessary.

Said formulations can also contain dyes, preservatives and additives to improve their smell and taste, for example oil of mint and eucalyptus oil and sweeteners, for example saccharin.

The pharmaceutical preparations mentioned can contain, as active principles, other active pharmaceutical agents as well as the compounds according to the present invention.

MODES FOR CARRYING OUT THE INVENTION

Up to now, a description of a general nature has been given of the compounds object of the present invention. With the help of the following examples a more detailed description is now given, with the aim of giving a better understanding of their objects, characteristics and functional advantages.

In the following examples will first of all be given the data necessary for synthesis of the compounds according to the present invention. There will then be given data regarding their pharmacological activity, using methods widely known to be valid. In particular, for the pressure tests, spontaneously hyper-tensive rats were used (SHR from the company Charles River), operated in such a way as to enable pressure to be read even when the animals were awake and free to move. In order to evaluate the analgesic activity, the Hot Plate and Writhing Tests were used. For the anti-inflammatory effect the test of carraginine edema was used. Finally, for immuno-modulating activity the evaluation of the stimulation of growth of human lymphocytes in culture was resorted to, after the addition of specific antigens. The results obtained for each synthesized compound are given at the end of each example.

For the components used in the examples, the following abbreviations have been adopted:

(S)-CytOEt=Ethyl-(S)-1,2,3,4-tetrahydro-9H-pyrido[3,4-b]indole-3-carboxylate (1)-Me-(S)-CytOMe=Methyl-(1)-Methyl-(S)-1,2,3,4-tetrahydro-9H-pyrido[3,4-b]indole-3-carboxylate (9)-Me-(S)-CytOMe=Methyl-(9)-Methyl-(S) -1,2,3,4-tetrahydro-9H-pyrido[3,4-b]indole-3-carboxylate (5)-Me-(S)-CytOMe=Methyl-(5)-Methyl-(S)-1,2,3,4-tetrahydro-9H-pyrido[3,4-b]indole-3-carboxylate 5-OH-(S)-CytOMe=Methyl-(5)-hydroxy-(S)-1,2,3,4-tetrahydro-9H-pyrido[3, 4-b]indole-3-carboxylate TrpH=Tryptamine CytH=Tryptoline (or: 1,2,3,4-tetrahydro-9H-pyrido[3,4-b]indole)

CypH=1,2,3,4-tetrahydro isoquinoline (L)-OmtOMe=Methyl-4-methoxy-(L)-phenylalaninate (L)-PhgOMe=Methyl-(L)-phenylglycinate (L)-Pme=(S)-(–)-2-amino-1-methoxy-3-phenylpropane 2-Fur=2-furoic acid (or: furan-2-carboxylic acid)

2-Tiof=2-thiophenic acid (or: thiophene-2-carboxylic acid)

2-Pyrrolyl=pyrrole-2-carboxylic acid

1-Me-2-Pyrrolyl=1-methyl-pyrrole-2-carboxylic acid

2-Indolyl=indole-2-carboxylic acid

1-Me-2-indolyl=1-methyl-indole-2-carboxylic acid

N-Me-(L)-Pro=N-methyl-(L)-Proline (L)-CypOMe=methyl-1,2,3,4-tetrahydro isoquinoline-3-carboxylate (1)-Me-(L) -CypOMe=Methyl-(1)-methyl-1,2,3,4-tetrahydro isoquinoline-3-carboxylate (6)-MeO-(L)-CypOMe=Methyl-(6)-methoxy-1,2,3,4-tetrahydro isoquinoline-3-carboxylate Cpe=1,2,3,4-tetrahydro isoquinoline-3-methoxy methyl (L)-Mep=(2)-methyl-(L)-Proline $\nabla^{3,4}$-(L)-Pro=3,4 dihydro-(L)-Proline (S)-Dhi=(S)-(–)-indoline-2-carboxylic acid (L)-Pip=(L)-pipecholinic-2-carboxylic acid (L)-Tia=(L)-(–)-thiazolidine-(4)-carboxylic acid (S)-Aza=(S)-(–)-azetidinic-2-carboxylic acid (S)-Tfc=(–)-tetrahydro furane-2-carboxylic acid.

EXAMPLE 1

Synthesis and pharmacological activity of Z-(L)-Pro-(L)-Ala-(S)-CytOEt (compound 1)

A suspension of 1.830 g (5.71 mmoles) of Z-(L)-Pro-(L)-AlaOH (Sigma) in 100 ml of anhydrous tetrahydrofuran (THF) was brought under argon atmosphere to a temperature of approximately −20° C. On stabilization of the temperature, the following were added under stirring in quick succession: 0.820 ml (6.27 mmoles) of isobutylchloroformate (IBCF) and 0.690 ml (6.28 mmoles) of 4-methylmorpholine (NMM), leaving the system under stirring for approximately 2 minutes. Then 0.850 g (6.29 mmoles) of anhydrous 1-hydroxybenzotriazole (HoBt) were added. The mixture was left under stirring for approximately 20 minutes, keeping the temperature under control at approximately −15° C. A solution was then added, precooled to −15° C. for 30 minutes, of 1.570 g (5.59 mmoles) of (S)-CytOEt.HCl (the free acid was prepared according to Brossi's method [A. Brossi, A. Forcella, S. Teitel: J.M.C. (1973), 16(4), 418] and the corresponding ethyl ester was prepared according to Chan's method [M. A. Brook, T. H. Chan: Synthesis, (1983) (3), 201]) and 0.620 ml (5.62 mmoles) of NMM in 30 ml of anhydrous N,N-dimethylformamide (DMF). Leaving the temperature of the system free to rise to room temperature, after approximately one hour, 0.690 ml (6.28 mmoles) of NMM were again added, maintaining stirring and static argon for a further 12 hours. The white precipitate was then filtered away and washed with a little anhydrous THF. The latter was put back into the reaction solution of a yellowish colour which, concentrated under vacuum to approximately one quarter of its original volume, was diluted four times with methylene chloride and was extracted in succession using 5% $NaHCO_3$ (4×30 ml); saturated aqueous NaCl (2×30 ml); 4% $KHSO_4$ (4×30 ml) and finally saturated aqueous NaCl (3×30 ml), discarding the aqueous phases. The organic phase extracted was left in a cool chamber under argon and on anhydrous $Na_2SO_4$ for 12 hours. The desiccant was then filtered away and the solution concentrated to a small volume under vacuum. The residual yellowish oil was taken up with 30 ml of a methanol/anhydrous ethyl ether mixture (5:1), obtaining a limpid, yellowish solution which, after elimination of the ethyl ether, was dripped slowly into an excess of cold water. The large amount of white precipitate thus obtained, after a couple of hours in a cold chamber, is filtered, washed using 20 ml of a water/methanol solution (10:1) and dried under vacuum on $P_2O_5$ for 24 hours. 2.0 g (65.45%) of an analytically pure whiteish solid were recovered.

This compound shows a good anti-hypertensive effect. At a dose of 4 mg/Kg i.p., the pressure values were reduced by 15–20%, and the effect was maintained for a number of hours.

At the same dose, a slight pain killing effect was also noted under the Hot Plate test.

From an immunological point of view, the compound increases the response of lymphocytes stimulated by phytohemoagglutinine (PHA).

The following compounds were prepared in a similar manner:

Z-(L)-Pro-(L)-Leu-(S)-CytOMe

Z-(L)-Pro-(L)-Leu-(1)-Me-(S)-CytOMe

Z-(L)-Pro-(L)-Leu-(9)-Me-(S)-CytOMe

Z-(L)-Pro-(L)-Ala-(1)-Me-(S)-CytoMe

Z-(L)-Pro-(L)-Ala-(5)-Me-(S)-CytOMe

Z-(L)-Pro-(L)-Ala-(9)-Me-(S)-CytOMe

Z-(L)-Pro-(L)-Ala-(1,5)-Me-(S)-CytOMe

Z-(L)-Pro-(L)-Ala-(5)-OH-(S)-CytOMe

Z-(L)-Pro-Gly-(S)-CytOMe

Z-(L)-Pro-Gly-(l)-Me-(S)-CytOMe

Z-(L)-Pro-(L)-Val-(l)-Me-(S)-CytOMe

Z-(L)-Pro-(L)-Val-(S)-CytOMe

EXAMPLE 2

Synthesis and pharmacological activity of Z-(L)-Pro-(L)-Ala-TrpH (compound 2)

A suspension of 1.500 g (4.68 mmoles) of Z-(L)-Pro-(L)-AlaOH (Sigma) in 60 ml of dry methylene chloride ($CH_2Cl_2$) was brought under argon atmosphere to a temperature of approximately −20° C. On stabilization of the temperature, the following were added under stirring in quick succession: 0.620 ml (4.74 mmoles) of isobutylchloroformate (IBCF) and 0.580 ml (4.77 mmoles) of N-methylpiperidine (NMP), leaving the system under stirring for approximately 2 minutes. A solution precooled to −15° C. for 30 minutes of 0.880 g (4.47 mmoles) of TrpH.HCl and 0.550 ml (4.52 mmoles) of NMP in 15 ml of anhydrous N,N-dimethylformamide (DMF) was then added to the white suspension. Under stirring, the temperature of the system was allowed to rise to room temperature. After approximately 3.5 hours of reaction, the white precipitate was filtered away and washed with a little $CH_2Cl_2$. The latter was put back into the reaction solution of a yellowish colour, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted was left in a cool chamber under argon and on anhydrous $Na_2SO_4$ for 24 hours. The desiccant was then filtered away and the solution concentrated to a small volume under vacuum. The residual yellowish liquid was dripped under stirring into 150 ml of petroleum ether (30/50), obtaining a rubbery grey precipitation. The solution was decanted and the residual mass was taken up with a minimum of $CH_2Cl_2$ and further purified by flash-chromatography in a normal phase ($SiO_2$, eluant $CH_2Cl_2$/n-Hexane/n-PrOH 10:1.5:0.5). Having collected and joined together the fractions of interest, most of the eluant was eliminated under vacuum and precipitation with an excess of n-Hexane takes place. There was a large amount of whiteish precipitate, slightly rubbery, which was filtered after a couple of hours and dried on $P_2O_5$ under vacuum for 24 hours. 1.300 g (62.8%) of an analytically pure whiteish solid were recovered.

On pressure, this compound has an activity comparable to that of compound 1. The immune response was also increased, but to a lesser extent than in the previous compound.

EXAMPLE 3

Synthesis and pharmacological activity of Z-(L)-Pro-(L)-Ala-CytH (compound 3)

A suspension of 1.500 g (4.68 mmoles) of Z-(L)-Pro-(L)-AlaOH (Sigma) in 70 ml of dry methylene chloride ($CH_2Cl_2$) was brought in an argon atmosphere to a temperature of approximately −20° C. On stabilization of the temperature, the following were added under stirring in quick succession: 0.620 ml (4.74 mmoles) of isobutylchloroformate (IBCF) and 0.580 ml (4.77 mmoles) of N-methylpiperidine (NMP), leaving the system under stirring for approximately 2 minutes. Adding 0.650 g (4.81 mmoles) of anhydrous 1-hydroxybenzotriazole (HOBT), the temperature was kept, under stirring, at approximately −15° C. for a further 20 minutes, then adding 0.780 g (4.53 mmoles) of CytH (Aldrich). Leaving the temperature of the system free to rise to room temperature, after approximately one hour another 0.580 ml (4.77 mmoles) of NMP were added. The mixture was left under stirring, static argon, out of the light, for 12 hours. The solid white precipitate was filtered away and washed with a little methylene chloride, which was put back into the reaction solution of a yellowish colour. This was extracted in succession using 5% $NaHCO_3$ (3×30 ml); saturated aqueous NaCl (2×30 ml); 4% $KHSC_4$ (3×30 ml) and finally saturated aqueous NaCl (3×30 ml), discarding the aqueous phases. The organic phase extracted was left in a cool chamber under argon and on anhydrous $Na_2SO_4$ for 24 hours. The desiccant was then filtered away and the solution concentrated to a small volume under vacuum, obtaining a residual yellowish oil which was taken up with anhydrous ethyl ether. The ether solution thus obtained was brought back to a dry state under vacuum and the residual yellow oil, taken up with the smallest possible volume of acetate mixture of ethyl/n-hexane (2:1) was purified by flash-chromatography in a normal phase ($SiO_2$, eluant ethyl acetate/n-hexane: 2/1.5). Having joined and concentrated the fractions of interest under vacuum a dense pale yellow oil was left which, when taken up with a minimum quantity of methanol, was precipitated in an excess of water, obtaining an abundant flocculent whiteish precipitate. After two hours rest in a cold chamber the off-white precipitate was filtered and dried under vacuum on $P_2O_5$ for 24 hours. 1.520 g (70.7%) of an analytically pure, slightly rubbery off-white solid were recovered.

The compound Z-(L)-Pro-(L)-Ala-CypH was prepared in a similar manner.

The compound shows a bland anti-hypertensive effect, at a dose of 8 mg/Kg/i.p.

EXAMPLE 4

Synthesis and pharmacological activity of Z-(L)-Pro-(L)-Ala-(L)-OmtOMe (compound 4)

A suspension of 1.600 g (5.00 mmoles) of Z-(L)-Pro-(L)-AlaOH (Sigma) in 70 ml of dry methylene chloride ($CH_2Cl_2$) was brought, under stirring and in an argon atmosphere, to the temperature of the ice and salt bath. The following were then added in succession: 0.850 g (5.03 mmoles) of commercial 1-hydroxybenzotriazole (HOBt) and 0.960 g (5.01 mmoles) of N-(dimethylaminopropyl)-N'-ethylcarbodiimide.HCl (EDC). Keeping the temperature under control, the mixture was left under stirring for 10 minutes and then the following were added in succession: 1.210 g (4.92 mmoles) of OmtOMe.HCl, prepared (according to Chan's method) from 4-methoxy-(L)-phenylalanine (Aldrich) and 0.550 ml (4.99 mmoles) of 4-methylmorpholine (NMM), maintaining the temperature for a further 2 hours. The mixture was then left under stirring and static argon for 12 hours with the temperature free to rise to room temperature. The solid white precipitate was filtered away and washed with a little $CH_2Cl_2$. The latter was put back into the filtered reaction solution, which was extracted in succession using 5% $NaHCO_3$ (3×30 ml); saturated aqueous NaCl (2×30 ml); 4% $KHSO_4$ (3×30 ml) and saturated aqueous NaCl (3×30 ml), discarding the aqueous phases. The organic phase extracted was left in a cool chamber under argon and on anhydrous $Na_2SO_4$ for 12 hours. The desiccant was then filtered away, the solution concentrated to a small volume and dripped under stirring into approximately 180 ml of dry petroleum ether (30/50), obtaining an abundant milk-white precipitation, which after a few hours at rest in a cold chamber was filtered and left for 12 hours under vacuum on $P_2O_5$. 2.020 g (80.2%) of an analytically pure milk-white solid were recovered.

The compound shows a bland anti-hypertensive effect, at a dose of 8 mg/Kg/i.v.. The immune response was also slightly increased.

EXAMPLE 5

Synthesis and pharmacological activity of Z-(L)-Pro-(L)-Ala-(L)-PhgOMe (compound 5)

A suspension of 1.500 g (4.68 mmoles) of Z-(L)-Pro-(L)-AlaOH (Sigma) in 60 ml of dry methylene chloride ($CH_2Cl_2$) was brought, under stirring and in an argon atmosphere, to the temperature of the ice and salt bath. The following were then added in succession: 0.800 g (4.73 mmoles) of commercial 1-hydroxybenzotriazole (HOBt) and 0.900 g (4.69 mmoles) of N-(dimethylaminopropyl)-N'-ethylcarbodiimide.HCl (EDC). Keeping the temperature under control, the mixture was left under stirring for 10 minutes and then the following were added in succession: 0.940 g (4.66 mmoles) of (L)-PhgOMe.HCl (Bachem) and 0.520 ml (4.72 mmoles) of 4-methylmorpholine (NMM), maintaining the temperature for a further 2 hours. The mixture was then left under stirring and static argon for 12 hours with the temperature free to rise to room temperature. The solid white precipitate was filtered away and washed with a little $CH_2Cl_2$. The latter was put back into the filtered reaction solution, which was extracted in succession using 5% $NaHCO_3$ (3×30 ml); saturated aqueous NaCl (2×30 ml); 4% $KHSO_4$ (3×30 ml) and finally saturated aqueous NaCl (2×30 ml), discarding the aqueous phases. The organic phase extracted was left in a cold chamber under argon and on anhydrous $Na_2SO_4$ for 12 hours. The desiccant was then filtered away, the solution concentrated to a small volume and the dense residual liquid was ground with anhydrous ethyl ether a number of times, decanting each time and discarding the ether phase. The residual solid was left for 24 hours under vacuum on $P_2O_5$. 1.630 g (74.8%) of an analytically pure powdery white solid were recovered.

The compound shows a bland anti-hypertensive effect, at a dose of 8 mg/Kg/i.p.. It also has a moderate analgesic effect when tested using the Hot Plate test.

The following compounds were prepared in a similar manner:

Z-(L)-Pro-(L)-Leu-(L)-PhgOMe
Z-(L)-Pro-(L)-Val-(L)-PhgOMe
Z-(L)-Pro-Gly-(L)-PhgOMe

EXAMPLE 6

Synthesis and pharmacological activity of Z-(L)-Pro-(L)-Ala-(L)-Pme (compound 6)

A suspension of 1.550 g (4.84 mmoles) of Z-(L)-Pro-(L)-AlaOH (Sigma) in 60 ml of dry methylene chloride ($CH_2Cl_2$) was brought, under stirring and under argon atmosphere, to the temperature of the ice and salt bath. The following were then added in succession: 0.820 g (4.85 mmoles) of commercial 1-hydroxybenzotriazole (HOBt) and 0.930 g (4.85 mmoles) of N-(dimethylaminopropyl)-N'-ethylcarbodiimide.HCl (EDC). Keeping the temperature under control, the mixture was left under stirring for 10 minutes and then the following were added in succession: 0.970 g (4.81 mmoles) of (L)-Pme.HCl (Fluka) and 0.530 ml (4.81 mmoles) of 4-methylmorpholine (NMM), maintaining, the temperature for a further 2 hours. The mixture was then left under stirring and static argon for 12 hours with the temperature free to rise to room temperature. The solid white precipitate was filtered away and washed with a little $CH_2Cl_2$. The latter was put back into the filtered reaction solution, which was extracted in succession using 5% $NaHCO_3$ (3×30 ml); saturated aqueous NaCl (2×30 ml); 4% $KHSO_4$ (3×30 ml) and finally saturated aqueous NaCl (2×30 ml), discarding the aqueous phases. The organic phase extracted was left in a cold chamber under argon and on anhydrous $Na_2SO_4$ for 12 hours. The desiccant was then filtered away, the solution concentrated to a small volume and dripped into 150 ml of dry petroleum ether (30/50), obtaining an abundant, slightly rubbery milk-white precipitate. This was left at rest in a cold chamber for a few hours and then the solid white precipitate was filtered under vacuum and ground with anhydrous ethyl ether, discarding the ether phase. The residual white solid was left for 24 hours under vacuum on $P_2O_5$, 1.870 g (80.1%) of an analytically pure white solid were recovered.

The compound has a good anti-hypertensive activity at a dose of 2 mg/Kg i.v.. After one hour the pressure was reduced by approximately 25%. The compound furthermore has a good analgesic activity, expressed in a 70% reduction of contorsions during the Writhing test, and extension of time (25%) in the Hot Plate test. The anti-inflammatory effect appears to be rather weak, while the increase in immunological activity was more consistent. The following compounds have been prepared in a similar manner:

Z-(L)-Pro-(L)-Leu-(L)-Pme
Z-(L)-Pro-(L)-Val-(L)-Pme
Z-(L)-Pro-Gly-(L)-Pme

EXAMPLE 7

Synthesis and pharmacological activity of Z-(L)-Pro-(L)-Ala-(1)-Me-(L)-TrpOMe (compound 7)

A suspension of 2.100 g (6.55 mmoles) of Z-(L)-Pro-(L)-AlaOH (Sigma) in 80 ml of dry methylene chloride ($CH_2Cl_2$) was brought, under argon atmosphere, to a temperature of approximately $-20°$ C. On stabilization of the temperature, the following were added in rapid succession: 0.850 ml (6.50 mmoles) of isobutylchloroformate (IBCF) and 0.790 ml (6.50 mmoles) of N-methylpiperidine (NMP), leaving the system under stirring for approximately 2 minutes. A solution pre-cooled to $-15°$ C. for 30 minutes of 1.700 g (6.32 mmoles) of TrpOMe.HCl, prepared (according to Chan's method) from 1-Me-(DL)-TrpOH (Aldrich) and 0.770 ml (6.33 mmoles) of NMP in 25 ml of anhydrous N,N-dimethylformamide (DMF) was then added to the white suspension. Under stirring, the temperature of the system was allowed to rise to room temperature. After approximately 4 hours of reaction, the white precipitate was filtered away and washed with a little $CH_2Cl_2$. The latter was put back into the reaction solution of a yellowish colour, which was extracted in succession using 5% $NaHCO_3$ (4×30 ml); saturated aqueous NaCl (2×30 ml); 4% $KHSO_4$ (4×30 ml) and finally saturated aqueous NaCl (3×30 ml), discarding the aqueous phases. The organic phase extracted was left in a cold chamber under argon and on anhydrous $Na_2SO_4$ for 24 hours. The desiccant was then filtered away and the solution concentrated to a small volume under vacuum. The residual yellowish liquid was dripped under stirring into 150 ml of n-hexane, obtaining a large amount of white precipitate, which was filtered after resting for several hours in a cold chamber, leaving the white solid under vacuum on $P_2O_5$ for 12 hours. 2.700 g (85.0%) of a white solid were recovered, which on analysis was shown to be Z-(L)-Pro-(L)-Ala-(1)-Me-(DL)-TrpOMe. The two diastereoisomers were separated by flash-chromatography in an inverse phase (resin $C_{18}$, eluant $H_2O/CH_3CN$ 60:40), collecting and uniting the fractions of interest. On elimination under vacuum of most of the organic phase, an abundant white flocculent precipitation was obtained which, after several hours at rest in a cold chamber, was filtered under vacuum. The filtered solid was dried for 24 hours on $P_2O_5$ under vacuum. 1.0 g (31.5%) of an analytically pure white solid corresponding to Z-(L)-Pro-(L)-Ala-(1)-Me-(L)-TrpOME were recovered.

The compound has a good anti-hypertensive effect, as at a dose of 2 mg/Kg i.v. a reduction of 10% in basic pressure was obtained in spontaneously hypertensive animals. The compound Z-(L)-Pro-(L)-Ala-(5)-Me-(L)-TrpOMe has been obtained in a similar manner.

EXAMPLE 8

Synthesis and pharmacological activity of 2-Fur-(L)-Leu-(L)-TrpOMe (compound 8)

A suspension of 1.0 g (2.72 mmoles) of (L)-Leu-(L)-TrpOMe.HCl (Novabiochem) in 60 ml of dry methylene chloride ($CH_2Cl_2$) was brought, under argon atmosphere, to the temperature of the ice and salt bath. 0.490 ml (6.07 mmoles) of dried pyridine were then added and, after approximately 10 minutes, a solution of 0.290 ml (2.96 mmoles) of 2-FurCl (Fluka) in 20 ml of dried $CH_2Cl_2$, freshly distilled, was added dropwise, controlling the temperature of the bath. On completing the additions, the reaction mixture was left under stirring, in an argon atmosphere and out of the light for approximately 4 hours. The mixture was then beaten in succession with 5% $NaHCO_3$ (3×30 ml), saturated aqueous NaCl (2×30 ml), 4% $KHSO_4$ (3×30 ml) and finally saturated aqueous NaCl (3×30 ml), discarding the aqueous phases. The organic phase extracted was left in a cold chamber under argon and anhydrous $Na_2SO_4$ for 12 hours. The desiccant was then filtered away and the organic solution, concentrated to a small volume under vacuum, was added dropwise under stirring to approximately 200 ml of dry petroleum ether (30/50). The milk-white precipitate, after several hours at rest in a cold chamber, was filtered under vacuum and washed with a small amount of $CH_2Cl_2$/petroleum ether mixture (1:10), discarding the organic solution. It was then left for 24 hours on $P_2O_5$ under vacuum. 0.750 g (65.0%) of an analytically pure off-white solid were recovered.

The compound shows a slight anti-hypertensive effect, at a dose of 4 mg/Kg i.v.. On human lymphocytes, the immune response was strongly stimulated even with small doses of peptide. The compound also shows a slight antiinflammatory effect.

The following compounds have been obtained in a similar manner:

2-Fur-(L)-Ala-(L)-TrpOMe
2-Fur-(L)-Val-(L)-TrpOMe
2-Fur-(L)-Ala-(S)-CytOMe
2-Fur-Gly-(L)-TrpOMe
2-Tiof-(L)-Leu-(L)-TrpOMe

EXAMPLE 9

Synthesis and pharmacological activity of 2-Pyrrolyl-(L)-Leu-(L)-TrpOMe (compound 9)

A suspension of 0.800 g (7.20 mmoles) of 2-pyrrolylcarboxylic acid (Aldrich) in 60 ml of dry methylene chloride ($CH_2Cl_2$) was brought, under argon, to the temperature of the ice and salt bath. The following were added successively under stirring: 1.380 g (7.20 mmoles) of N-(dimethylaminopropyl)-N'-ethylcarbodiimide.HCl (EDC) and 1.170 g (7.21 mmoles) of commercial 1-hydroxybenzotriazole (HOBt). Maintaining the temperature of the bath, after 10 minutes a further 2.650 g (7.20 mmoles) of (L)-Leu-(L)-TrpOMe.HCl (Novabiochem) and 0.800 ml (7.26 mmoles) of N-methylmorpholine were added, leaving the reaction mixture under agitation, in an argon atmosphere and out of the light for 12 hours. The white precipitate was then filtered away and washed with a little $CH_2Cl_2$. The latter was put back into the reaction solution of a brownish-yellow colour, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phase. The organic phase extracted was left under argon and out of the light for 12 hours on anhydrous $Na_2SO_4$. The desiccant was then filtered away, the solution concentrated to a small volume under vacuum and the residual yellow oil, taken up with the smallest possible amount of a chloroform/acetone mixture (3:1), was purified using flash-chromatography in a normal phase ($SiO_2$, eluant $CHCl_3$/acetone: 5.5/1). The chromatographic fractions, joined together and concentrated to a small volume, were added dropwise under stirring to 300 ml of petroleum ether (30/50), obtaining an abundant milk-white precipitate. After several hours at rest in a cold chamber, the off-white solid is filtered and left for 24 hours under vacuum on KOH in drops, out of the light. 1.450 g (47.4%) of an analytically pure dirty white solid were recovered.

The compound shows a slight effect on pressure, and gives a bland reduction of inflammatory responses. The following compounds have been prepared in a similar manner:

1-Me-2-Pyrrolyl-(L)-Leu-(L)-TrpOMe
1-Me-2-Indolyl-(L)-Leu-(L)-TrpOMe
2-Indolyl-(L)-Leu-(L)-TrpOMe

EXAMPLE 10

Synthesis and pharmacological activity of N-Me-(L)-Pro-(L)-Leu-(L)-TrpOMe.HCl (compound 10)

A suspension of 1.0 g (7.74 mmoles) of N-Me-(L)-Pro,OH (Sigma) in 60 ml of dry methylene chloride ($CH_2Cl_2$)

was brought, in an argon atmosphere, to the temperature of an ice and salt bath. The following were then added in succession: 1.250 g (7.74 mmoles) of commercial 1-hydroxybenzotriazole (HOBt) and 1.600 g (7.75 mmoles) of N,N'-dicyclohexylcarbodiimmide (DCC), leaving the system under stirring and maintaining control of the temperature for a further 30 minutes. To the reaction mixture was then added with 2.800 g (7.61 mmoles) of (L)-Leu-(L)-TrpOMe.HCl (Novabiochem) and 0.840 ml (7.62 mmoles) of 4-methylmorpholine (NMM), leaving the system under stirring for 12 hours with the temperature free to rise to room temperature. The fine white precipitate was then filtered away and washed with a little $CH_2Cl_2$. The latter was put back into the filtered reaction solution, which was concentrated under vacuum to approximately half its original volume, filtering away the new white precipitate. It was then extracted in succession using 5% $NaHCO_3$ (3×30 ml) and saturated aqueous NaCl (2×30 ml), discarding the aqueous phases. The organic phase was then extracted with acetate buffer at pH 4 (3×30 ml), discarding the organic phase. The aqueous phase was brought to pH 6 and extracted using $CH_2Cl_2$ (3×30 ml). The organic phase, extracted with saturated aqueous NaCl (2×30 ml), was left in a cold chamber, under argon atmosphere and anhydrous $Na_2SO_4$ for 24 hours. The desiccant was then filtered away, the organic solution concentrated to a small volume and the residual yellowish liquid added dropwise under energetic stirring to an excess of dry petroleum ether (30/50), obtaining an abundant white precipitate. After several hours in a cold chamber the white solid was filtered and, taken up at the limit of solubility with anhydrous dioxane, was precipitated again in an excess of a solution of 1.0M of gaseous HCl in anhydrous ethyl ether. After leaving the suspension to rest in a cold chamber for approximately 1 hour, the excess of acid was eliminated under a flow of dry nitrogen, then adding a large excess of anhydrous ethyl ether. The abundant fine milk-white precipitation, filtered under vacuum and washed in a little anhydrous ethyl ether, was left for 24 hours under vacuum on $P_2O_5$. 2.550 g (70.0%) of an analytically pure semi-crystalline white solid were recovered.

The compound has an excellent anti-hypertensive effect, and at a dose of 2 mg/Kg i.v. pressure was reduced by 15–20%. The immune response was slightly increased, and the substance also shows a low analgesic effect. The following compounds have been prepared in a similar manner:

N-Me-(L)-Pro-(L)-Ala-(L)-TrpOMe.HCl
N-Me-(L)-Pro-(L)-Val-(L)-TrpOMe.HCl
N-Me-(L)-Pro-(L)-Ala-(S)-CytOMe.HCl
N-Me-(L)-Pro-Gly-(L)-TrpOMe.HCl

EXAMPLE 11

Synthesis and pharmacological activity of Z-(L)-Pro-(L)-Ala(L)-CypOMe (compound 11)

A suspension of 1.600 g (5.0 mmoles) of Z-(L)-Pro-(L)-AlaOH (Sigma) in 80 ml of dry methylene chloride ($CH_2Cl_2$) was brought in an argon atmosphere to a temperature of approximately −20° C. On stabilization of the temperature, the following were added in quick succession: 0.670 ml (5.13 mmoles) of isobutylchloroformate (IBCF) and 0.570 ml (5.17 mmoles) of 4-methylmorpholine (NMM), leaving the system under stirring for approximately 2 minutes.

Adding 0.700 g (5.18 mmoles) of anhydrous 1-hydroxybenzotriazole (HOBT), the temperature was kept at approximately −15° C for a further 20 minutes. A solution, pre-cooled to approximately −15° C. for 30 minutes, of 1.100 g (4.83 mmoles) of (L)-CypOMe.HCl, prepared (according to Chan's method) from (L)-1,2,3,4-tetrahydro-3-isoquinolinic acid hydrochlorate (Bachem) and 0.540 ml (4.90 mmoles) of NMM in 20 ml of anhydrous N,N-dimethylformamide (DMF) was then added to the reaction mixture. Leaving the temperature of the bath free to rise to room temperature, after approximately one hour a further 0.570 ml (5.17 mmoles) of NMM were added, continuing stirring and static argon for a further 12 hours. The white precipitate was then filtered away and washed with a little $CH_2Cl_2$. The latter was put back into the reaction solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted was left in a cold chamber under argon and on anhydrous $Na_2SO_4$ for 24 hours. The desiccant was then filtered away, the organic solution concentrated to a small volume under vacuum, and the residual thick oil was taken up with ethyl acetate at the limit of solubility and added dropwise to an excess of a mixture (5:1) of n-hexane/ethyl ether. An initial oily white precipitate was obtained which, after 24 hours in a cold chamber, thickens. After decanting and discarding the precipitation solution the residual solid was taken up with the smallest possible amount of absolute ethyl alcohol and the resulting solution was added dropwise to a large excess of water. An abundant white precipitation was obtained which, after 12 hours in a cold chamber, was filtered and left under vacuum on $P_2O_5$ for 24 hours. 1.260 g (52.8%) of an analytically pure, slightly rubbery, dirty white solid were recovered.

The compound shows a slight anti-hypertensive effect, together with a moderate anti-inflammatory effect.

The following compounds were prepared in a similar manner:

Z-(L)-Pro-(L)-Leu-(L)-CypOMe
Z-(L)-Pro-(L)-Val-(L)-CypOMe
Z-(L)-Pro-Gly-(L)-CypOMe
Z-(L)-Pro-(L)-Ala-(l)-Me-(L)-CypOMe
Z-(L)-Pro-(L)-Ala-(6)-MeO-(L)-CypOMe
Z-(L)-Pro-(L)-Ala-(1)-Me-(6)-MeO-(L)-CypOMe
Z-(L)-Pro-(L)-Leu-(1)-Me-(L)-CypOMe
Z-(L)-Pro-(L)-Ala-(L)-Cpe

EXAMPLE 12

Synthesis and pharmacological activity of Boc-(L)-Mep-(L)-Leu-(L)-TrpOMe (compound 12)

A suspension of 1.150 g (5.02 mmoles) of N-tert.butyloxycarbonyl-(2)-methyl-(L)-proline (abbreviation Boc-(L)-MepOH, prepared according to the method of Thaisrivongs [S. Thaisrivongs, D. T. Pais, J. A. Lawson, S. R. Turner, D. W. Harris: J.M.C. 30, 536 (1987)] using 2-methyl-(L)-proline, prepared according to the method of Seebach [D. Seebach, M. Boes, R. Naif, W. B. Schwerzer; J.A.C.S. 105, 5390 (1983)]) in 60 ml of dry methylene chloride ($CH_2Cl_2$) was brought under argon atmosphere to a temperature of approximately −20° C. On stabilization of the temperature, the following were added in quick succession: 0.670 ml (5.13 mmoles) of isobutylchloroformate (IBCF) and 0.630 ml (5.18 mmoles) of 4-methylpiperidine (NMP), leaving the system under stirring for approximately 2 minutes. A solution, pre-cooled to approximately −15° C. for 30 minutes of 1.780 g (4.84 mmoles) of (L)-Leu-(L)-TrpOMe.HCl (Novabiochem) and 0.600 ml (4.93 mmoles) of NMP in 25 ml of anhydrous N,N-dimethylformamide (DMF) was then added to the reaction mixture, leaving, under stirring and static argon, the temperature of the bath free to rise to room temperature. After approximately 5 hours of reaction, the white precipitate was then filtered away and washed with a little $CH_2Cl_2$. The latter was put back into the pale yellow coloured organic solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume under vacuum, was purified using flash-chromatography in a normal phase ($SiO_2$, eluant $CH_2Cl_2$/n-hexane: 4/1). The chromatographic fractions of interest, joined together and concentrated to a small volume, were precipitated by a large excess of n-hexane, obtaining an abundant white precipitate which, after several hours at rest in a cold chamber, was filtered, discarding the organic solution. The residual solid was left for 24 hours under vacuum on KOH in drops. 1.450 g (55.2%) of an analytically pure pseudo-crystalline white solid were recovered.

The compound shows a bland anti-hypertensive effect, and also shows reduction of the inflammatory response (edema from carrageenin).

EXAMPLE 13

Synthesis and pharmacological activity of Boc-$\nabla^{3,4}$-(L)-Pro-(L)-Leu-(L)-TrpOMe (compound 13)

A suspension of 1.000 g (4.67 mmoles) of N-tert.butyloxycarbonyl-3.4-dehydro-(L)-proline (abbreviation Boc-$\nabla^{3,4}$-(L)-Pro, (Bachem)) in 60 ml of dry methylene chloride ($CH_2Cl_2$) was brought under argon atmosphere to a temperature of approximately −20° C. On stabilization of the temperature, the following were added in quick succession: 0.630 ml (4.82 mmoles) of isobutylchloroformate (IBCF) and 0.590 ml (4.85 mmoles) of 4-methylpiperidine (NMP), leaving the system under stirring for approximately 2 minutes. A solution, precooled to approximately −15° C. for 30 minutes, of 1.670 g (4.54 mmoles) of (L)-Leu-(L)-TrpOMe.HCl (Novabiochem) and 0.560 ml (4.61 mmoles) of NMP in 25 ml of anhydrous N,N-dimethylformamide (DMF) was then added to the reaction mixture, leaving, under stirring and static argon, the temperature of the bath free to rise to room temperature. After approximately 4.5 hours of reaction, the white precipitate was filtered away and washed with a little $CH_2Cl_2$. The latter was put back into the pale yellow coloured organic solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume, was purified using flash-chromatography in a normal phase ($SiO_2$, eluant $CH_2Cl_2$/methanol 2%). The chromatographic fractions of interest, joined together and concentrated to a small volume, were precipitated by a large excess of n-hexane, obtaining an abundant white precipitate which, after several hours at rest in a cold chamber, was filtered, discarding the organic solution. The residual solid was left for 24 hours under vacuum on KOH in drops. 1.440 g (60.2%) of an analytically pure pseudo-crystalline white solid were recovered.

The compound was slightly anti-hypertensive, and slightly increases the immune response. The following compounds have been prepared in a similar manner:

Boc-$\nabla^{3,4}$-(L)-Pro-(L)-Ala-(L)-TrpOMe
Boc-$\nabla^{3,4}$-(L)-Pro-(L)-Val-(L)-TrpOMe
Boc-$\nabla^{3,4}$-(L)-Pro-(L)-Ala-(S)-CytOMe
Boc-$\nabla^{3,4}$-(L)-Pro-Gly-(L)-TrpOMe

EXAMPLE 14

Synthesis and Pharmacological activity of Z-(S)-Dhi-(L)-Leu-(L)-TrpOMe (compound 14)

A suspension of 1.500 g (5.04 mmoles) of N-benzyloxycarbonyl-(S)-(−)-indoline-2-carboxylic acid (abbreviation Z-(S)-DhioH, prepared from (S)-(−)-indoline-2-carboxylic acid (Aldrich) according to the method of Wunsch [E. Wunsch, W. Graf, O. Keller, W, Keller, G. Wersin: Synthesis, (11), 958 (1986)]) in 80 ml of dry methylene chloride ($CH_2Cl_2$) was brought under argon atmosphere to a temperature of approximately −20° C. On stabilization of the temperature, the following were added in quick succession: 0.680 ml (5.20 mmoles) of isobutylchloroformate (IBCF) and 0.580 ml (5.26 mmoles) of 4-methylmorpholine (NMM), leaving the system under stirring for approximately 2 minutes. A solution, precooled to approximately −15° C. for 30 minutes, of 1.840 g (5.00 mmoles) of (L)-Leu-(L)-TrpOMe.HCl (Novabiochem) and 0.560 ml (5.08 mmoles) of NMM in 25 ml of anhydrous N,N-dimethylformamide (DMF) was then added, leaving, under stirring and static argon, the temperature of the bath free to rise to room temperature. After approximately 5 hours of reaction, the white precipitate was then filtered away and washed with a little $CH_2Cl_2$. The latter was put back into the pale yellow coloured organic solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume, was added dropwise under stirring to 200 ml of dry petroleum ether (30/50), obtaining an abundant white precipitate which, after several hours at rest in a cold chamber, was filtered, discarding the organic solution. The residual solid was left for 24 hours under vacuum on $P_2O_5$. 2.440 g (79.9%) of an analytically pure white solid were recovered.

The compound induces a bland reduction of pressure, and has a moderate analgesic effect. The following compounds have been prepared in a similar manner:

Z-(S)-Dhi-(L)-Ala-(L)-TrpOMe
Z-(S)-Dhi-(L)-Val-(L)-TrpOMe
Z-(S)-Dhi-(L)-Ala-(S)-CytOMe
Z-(S)-Dhi-Gly-(L)-TRpOMe

EXAMPLE 15

Synthesis and pharmacological activity of Z-(L)-Pip-(L)-Leu-(L)-TrPOMe (compound 15)

A suspension of 1.300 g (4.94 mmoles) of N-benzyloxycarbonyl-(L)-pipecoline-2-carboxylic acid (abbreviation Z-(L)-PipOH, prepared from (L)-pipecholine-2-carboxylic acid (Aldrich) according to the method of Wunsch) in 60 ml of dry methylene chloride ($CH_2Cl_2$) was brought under argon atmosphere to a temperature of approximately −20° C. On stabilization of the temperature, the following were added in quick succession: 0.670 ml (5.13 mmoles) of isobutylchloroformate (IBCF) and 0.630 ml (5.18 mmoles) of 4-methylpiperidine (NMP;), leaving the system under stirring for approximately 2 minutes. A solution, pre-cooled to approximately −15° C for 30 minutes, of 1.730 g (4.70 mmoles) of (L)-Leu-(L)-

TrpOMe.HCl (Novabiochem) and 0.580 ml (4.77 mmoles) of NMP in 25 ml of anhydrous N,N-dimethylformamide (DMF) was then added, leaving, under stirring and static argon, the temperature free to rise to room temperature. After approximately 3,5 hours of reaction, the white precipitate was filtered away and washed with a little $CH_2Cl_2$. The latter was put back into the pale yellow coloured organic solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume, was added dropwise under stirring to 200 ml of dry petroleum ether (30/50), obtaining an abundant milk-white precipitate which, after several hours at rest in a cold chanber, was filtered and left for 24 hours under vacuum on $P_2O_5$. 2.300 g (84.8%) of an analytically pure white solid were recovered.

The compound shows a good anti-hypertensive effect, with a decrease of pressure valued of up to 30% after 2 mg/Kg i.v. The reduction of the inflammatory response also appears to be consistent, while a slight increase in immune response can be seen.

The following compounds have been prepared in a similar manner:

Z-(L)-Pip-(L)-Ala-(L)-TrpOMe
Z-(L)-Pip-(L)-Val-(L)-TrpOMe
Z-(L)-Pip-(L)-Ala-(S)-CytOMe
Z-(L)-Pip-Gly-(L)-TrpOMe
Boc-(L)-Tia-(L)-Leu-(L)-TrpOMe

EXAMPLE 16

Synthesis and pharmacological activity of Z-(L)-Hyp-(L)-Leu-(L)-TrpOMe (compound 16)

A suspension of 1.600 g (4.98 mmoles) of N-benzyloxycarbonyl-O-tButyl-trans-hydroxy-(L)-proline (abbreviation Z-O-tBu-(L)-HypOH, (Bachem)) in 70 ml of dry tetrohydrofuran (THF) was brought under argon atmosphere to a temperature of approximately −20° C. On stabilization of the temperature, the following were added in quick succession: 0.670 ml (5.13 mmoles) of isobutylchloroformate (IBCF) and 0.570 ml (5.17 mmoles) of 4-methylmorpholine (NMM), leaving the system under stirring for approximately 2 minutes. A solution, precooled to approximately −15° C. for 30 minutes, of 1.800 g (4.89 mmoles) of (L)-Leu-(L)-TrpOMe.HCl (Novabiochem) and 0.540 ml (4.90 mmoles) of NMP in 25 ml of anhydrous N,N-dimethylformamide (DMF) was then added, leaving, under stirring and static argon, the temperature free to rise to room temperature. After approximately 5 hours of reaction, the white precipitate was filtered away and washed with a little THF. The latter was put back into the pale yellow coloured organic solution, which, after having been concentrated under vacuum and taken up with three times the volume of methyl chloride, was extracted in succession using 5% $NaHCO_3$ (3×30 ml); saturated aqueous NaCl (2×30 ml); 4% $KHS_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume, was ground with an excess of anhydrous ethyl ether. The solid precipitate, after filtering, was taken up in the smallest possible quantity of ethyl acetate (AcOEt) and purified on an alumina column (eluant AcOEt/n-hexane: 5/1). The chromatographic fractions of interest, after being recovered and concentrated to a small volume, were precipitated with dry petroleum ether (30/50), obtaining a heavy white solid which, after several hours, was filtered and taken up with anhydrous dioxane. The solution thus obtained was treated under stirring and at the temperature of the ice bath with a solution of 4N gaseous HCl in anhydrous dioxane, in the presence of N-methylindole. After approximately 30 minutes the excess of gaseous HCl was eliminated under a flow of $N_2$, the residue was concentrated under vacuum and precipitated with a large excess of a mixture (1:1) of anhydrous ethyl ether/dry n-hexane, obtaining an abundant milk-white precipitation which, after several hours at rest, was filtered and left overnight under vacuum on $P_2O_5$. 1.500 g (53.0%) of an analytically pure heavy white solid were recovered.

The compound shows a bland anti-hypertensive action, joined to a modest analgesic effect.

EXAMPLE 17

Synthesis and pharmacological activity of Z-(S)-Aze-(L)-Leu-(L)-TrpOMe (compound 17)

A suspension of 1.200 g (5.10 mmoles) of N-benzyloxycarbonyl-(S)-(−)-2-azetidine-carboxylic acid (abbreviation Z-(S)-AzeOH, prepared from (S)-(−)-2-azetidinecarboxylic acid (Aldrich) according to the method of Wunsch) in 60 ml of dry methylene chloride ($CH_2Cl_2$) was brought in an argon atmosphere to a temperature of approximately −20° C. On stabilization of the temperature, the following were added in quick succession: 0.690 ml (5.27 mmoles) of isobutylchloroformate (IBCF) and 0.650 ml (5.34 mmoles) of 4-methylpiperidine (NMP), leaving the system under stirring for approximately 2 minutes. A solution, pre-cooled to approximately −15° C. for 30 minutes, of 1.850 g (5.03 mmoles) of (L)-Leu-(L)-TrpOMe.HCl (Novabiochem) and 0.620 ml (5.10 mmoles) of NMP in 25 ml of anhydrous N,N-dimethylformamide (DMF) was then added, leaving, under stirring and static argon, the temperature free to rise to room temperature. After approximately 3.5 hours of reaction, the white precipitate was filtered away and washed with a little $CH_2Cl_2$. The latter was put back into the pale yellow coloured organic solution, which was extracted in succession using 5% $NaHCO_3$ (3×30 ml); saturated aqueous NaCl (2×30 ml); 4% $KHSO_4$ (3×30 ml) and finally saturated aqueous NaCl (3×30 ml), discarding the aqueous phases. The organic phase extracted, of a pale yellow colour, was left in a cold chamber under argon and on anhydrous $Na_2SO_4$ for 12 hours. The desiccant was then filtered away and the organic solution, concentrated to a small volume, leaves a dense residual oil which, when taken up with a minimum amount of $CH_2Cl_2$, was purified using flash-chromatography in a normal phase ($SiO_2$, eluant $CH_2Cl_2$/n-hexane: 2/1). The chromatographic fractions of interest were concentrated to a small volume and ground with anhydrous ethyl ether. The whiteish solid thus obtained was filteres and left for 24 hours under vacuum on $P_2O_5$. 2.040 g (75.0%) of an analytically pure rubbery white solid were recovered.

The compound shows a slight anti-hypertensive effect nd bland anti-inflammatory activity. The following compounds have been prepared in a similar manner:

Z-(S)-Aze-(L)-Ala-(L)-TrpOMe
Z-(S)-Aze-(L)-Val-(L)-TrpOMe
Z-(S)-Aze-(L)-Ala-(S)-CytOMe
Z-(S)-Aze-Gly-(L)-TrpOMe

EXAMPLE 18

Synthesis and pharmacological activity of (S)-Tfc-(L)-Leu-(L)-TrpOMe (compound 18)

A suspension of 0.500 g (5.21 mmoles) of (−)tetrahydrofuran-2-carboxylic acid (Aldrich) in 50 ml of dry methylene chloride (CH$_2$Cl$_2$) was brought under argon atmosphere to the temperature of an ice and salt bath.

The following were then added in succession under stirring: 0.880 g (5.21 mmoles) of commercial hydroxybenzotriazole (HOBt) and 1.070 g (5.19 mmoles) of N.N'-dicyclohexylcarbodiimide (DCC). After 10 minutes, a further 1.900 g (5.16 mmoles) of (L)-Leu-(L)-TrpOMe.HCl (Novabiochem) and 0.570 ml (5.17 mmoles) of 4-methylmorpholine (NMM) were added, maintaining the temperature of the bath for a further 2 hours. The mixture was then left, under static argon, out of the light, and with the temperature free to rise to room temperature, under stirring for 12 hours. The white precipitate was then filtered away and washed with a little CH$_2$Cl$_2$. The latter was put back into the pale yellow coloured filtered reaction solution, which was dried out under vacuum. The yellowish solid thus obtained was ground with an excess of water and the aqueous solution, after extraction with ethyl acetate, was treated under stirring for 12 hours with ion-exchange resin Bio-Rad AG-501 X8 (D). On filtering away the resin, the aqueous solution was freeze-dried and the white solid thus recovered was ground with anhydrous ethyl ether, discarding the organic phase after decanting. The analytically pure white solid thus obtained (1.660 g, 74.8%) was separated into its two diastereoisomers by flash-chromatography in an inverted phase (resin C$_{18}$, eluant CH$_3$CN 30/H$_2$O 70 v/v), recovering the fractions of interest which, when joined together, concentrated and freeze-dried in their turn, give 0.580 g (34.9% with respect to the pure diastereoisomeric pair) of an analytically pure white solid.

The compound shows a bland anti-hypertensive effect, and stimulates the immune response in a moderate manner.

EXAMPLE 19

Synthesis and pharmacological activity of Z-(L)-Pyr-(L)-Leu-(L)-TrpOMe (compound 19)

A suspension of 1.300 g (4.94 mmoles) of N-benzyloxycarbonyl-(L)-pyroglutammic acid (abbreviation Z-(L)-PyrOH (Sigma) in 60 ml of dry methylene chloride (CH$_2$Cl$_2$) was brought under argon atmosphere to a temperature of approximately −20° C. On stabilization of the temperature, the following were added in succession: 0.670 ml (5.13 mmoles) of isobutylchloroformate (IBCF) and 0.630 ml (5.18 mmoles) of 4-methylpiperidine (NMP), leaving the system under stirring for approximately 2 minutes. A solution, pre-cooled to approximately −15° C. for 30 minutes, of 1.810 g (4.92 mmoles) of (L)-Leu-(L)-TrpOMe.HCl (Novabiochem) and 0.600 ml (4.94 mmoles) of NMP in 20 ml of anhydrous N,N-dimethylformamide (DMF) was then added, leaving the mixture under stirring and static argon for 12 hours with the temperature free to rise to room temperature. After approximately 4.0 hours of reaction, the white solid was filtered away and washed with a little CH$_2$Cl$_2$. The latter was put back into the reaction solution, which was extracted in succession using 5% NaHCO$_3$ (3×20 ml); saturated aqueous NaCl (1×20 ml); 4% KHSO$_4$ (3×20 ml) and finally saturated aqueous NaCl (2×20 ml), discarding the aqueous phases. The organic solution extracted was left in a cold chamber under argon and on anhydrous Na$_2$SO$_4$ for 12 hours. The desiccant was then filtered away and the solution concentrated to a small volume under vacuum. The dense residual oil was ground twice with anhydrous ethyl ether, obtaining a solidification of the oil itself. The solid thus obtained was taken up with 40 ml of dry CH$_2$Cl$_2$ and the solution was added dropwise under stirring to 200 ml of anhydrous ethyl ether, obtaining a milk-white precipitate which, after several hours at rest in a cold chanber, was filtered and left for 24 hours under vacuum on P$_2$O$_5$. 1.850 g (65.2%) of an analytically pure, slightly rubbery white solid were recovered.

The compound shows a slight anti-hypertensive effect, joined to a fair anti-inflammatory activity. The following compounds have been prepared in a similar manner:

Z-(L)-Pyr-(L)-Ala-(L)-TrpOMe

Z-(L)-Pyr-(L)-Val-(L)-TrpOMe

Z-(L)-Pyr-Gly-(L)-TrpOMe

EXAMPLE 20

Synthesis and pharmacological activity of Z-(L)-Pyr-(L)-Leu-(S)-CytOMe (compound 20)

A suspension of 2.870 g (5.00 mmoles) of the 2,4,5 trichlorophenol ester of Z-(L)-Pyr-(L)-LeuOH acid (ester prepared according to Morley's method [J. S. Morley, J.C.S., 2410 (1967)] from the Z-(L)-Pyr-(L)-LeuOH free acid, prepared according to the method of Klieger [E. Klieger, H. Gibian, Liebigs Ann. Chem. 649, 183 (1961)]) in 60 ml of anhydrous tetrahydrofuran (THF) was brought under stirring and in an argon atmosphere to the temperature of an ice and salt bath. On stabilization of the temperature, a pre-cooled solution of 1.270 g (5.51 mmoles) of methyl-(S)-1,2,3,4-tetrahydro-9H-pyrido-[3,4-b]-indole-3-carboxylate (abbreviation (S)-CytOMe, prepared by partition between 5% NaHCO$_3$ and ethyl acetate, with the organic phase left to dry, after partition, for 12 hours on anhydrous Na$_2$SO$_4$, from the corresponding hydrochloride, prepared as previously described for Z-(L)-Pro-(L)-Ala-(S)-CytOMe) in 40 ml of AcOEt. The temperature of the bath was kept under control for approximately one hour and then, leaving the temperature free to rise to room temperature, the mixture was left under stirring for a further 24 hours. The reaction mixture was then concentrated to a small volume and added dropwise under stirring to approximately 200 ml of anhydrous ethyl ether (Et$_2$O), obtaining an abundant white precipitation which, after being left to rest for several hours in a cold chamber, was filtered under vacuum, discarding the ethyl solution. The solid obtained, white in colour, was ground twice more with anhydrous Et$_2$O and then once with 30 ml of 5% NaHCO$_3$, discarding each time the filtered solutions. The solid was then left under vacuum on P$_2$O$_5$ for 24 hours. 2.580 g (85.0%) of an analytically pure powdery white solid were recovered.

The compound shows a bland anti-hypertensive activity, joined to a fair anti-inflammatory activity.

The following compounds have been prepared in a similar manner:

Z-(L)-Pyr-(L)-Ala-(S)-CytOMe

Z-(L)-Pyr-(L)-Val-(S)-CytOMe

Z-(L)-Pyr-(L)-Leu-(1)-Me-(S)-CytOMe

Z-(L)-Pyr-(L)-Ala-(l)-Me-(S)-CytOMe

Z-(L)-Pyr-(L)-Val-(1)-Me-(S)-CytoMe

Z-(L)-Pyr-(L)-Leu-(9)-Me-(S)-CytoMe

Z-(L)-Pyr-Gly-(S)-CytOMe

EXAMPLE 21

Synthesis and pharmacological activity of Z-(L)-Pyr-(L)-Leu-(S)-CyPOMe (compound 21)

A suspension of 2.500 g (4.36 mmoles) of the 2,4,5-trichlorophenol ester of Z-(L)-Pyr-(L)-LeuOH acid (ester prepared according to Morley's method from the Z-(L)-Pyr-(L)-LeuOH free acid, prepared according to the method of Klieger) in 60 ml of anhydrous tetrahydrofuran (THF) was brought under stirring and in an argon atmosphere to the temperature of an ice and salt bath. On stabilization of the temperature, a pre-cooled solution in 30 ml of AcOEt of 0.920 g (4.81 mmoles) of (L)-CypOMe, prepared by partition between 5% $NaHCO_3$ and ethyl acetate, with the organic phase left to dry, after partition, for 12 hours on anhydrous $Na_2SO_4$, from the corresponding hydrochloride, prepared as previously described for Z-(L)-Pro-(L)-Ala-(L)-CypOMe). The temperature of the bath was kept under control for approximately one hour and then, leaving the temperature free to rise to room temperature, the mixture was left under stirring for a further 24 hours. The reaction mixture was then concentrated to a small volume and the dense residual oil was ground three times with 50 ml of anhydrous n-hexane, discarding the solutions. A rubbery, yellowish-white solid was recovered which, taken up in a minimum quantity of methyl chloride, was further purified by flash-chromatography in a normal phase ($SiO_2$, eluant $CH_2Cl_2$). Having recovered, united and concentrated to a small volume the chromatographic fractions of interest, these were added dropwise to 100 ml of anhydrous n-hexane, obtaining a rubbery white solid which tends to solidify over a period of time. After 24 hours in a cold chamber the organic solution was decanted and the residual solid was left under vacuum on $P_2O_5$ for 12 hours. 1.780 g (74.3%) of an analytically pure, slightly rubbery heavy white solid were recovered.

The compound shows a slight anti-hypertensive activity, together with a good immuno-stimulating activity.

The following compounds have been prepared in a similar manner:

Z-(L)-Pyr-(L)-Ala-(S)-CypOMe

Z-(L)-Pyr-(L)-Val-(S)-CypOMe

Z-(L)-Pyr-(L)-Val-(1)-Me-(L)-CypOMe

Z-(L)-Pyr-(L)-Leu-(1)-Me-(L)-CypOMe

Z-(L)-Pyr-(L)-Ala-(1)-Me-(L)-CypOMe

Z-(L)-Pyr-(L)-Leu-(6)-MeO-(L)-CypOMe

Z-(L)-Pyr-Gly-(6)-MeO-(L)-CypOMe

Z-(L)-Pyr-Gly-(L)-CypOMe

Z-(L)-Pyr-(L)-Leu-(L)-Cpe

EXAMPLE 22

Synthesis and pharmacological activity of (L)-Pyr-Gly-(L)-PhgOMe (compound 22)

A suspension of 1.830 g (5.00 mmoles) of the 2,4,5 trichlorophenol ester of (L)-Pyr-GlyOH acid (ester prepared according to Morley's method from the (L)-Pyr-GlyOH free acid [Novabiochem]) in 60 ml of dry methyl chloride ($CH_2Cl_2$) was brought under stirring and in an argon atmosphere to the temperature of an ice and salt bath. On stabilization of the temperature, a pre-cooled solution of 0.910 mg (5.51 mmoles) of (L)-PghOMe (prepared by partition between 5% $NaHCO_3$ and $CH_2Cl_{21}$ with the organic phase left to dry, after partition, for 12 hours on anhydrous $Na_2SO_4$, from the corresponding hydrochloride, (L)-PhgOMe.HCl [Bachem]) in 40 ml of $CH_2Cl_2$. The temperature of the bath was kept under control for approximately one hour and then, leaving the temperature free to rise to room temperature, the mixture was left under stirring for a further 24 hours. The reaction mixture was then concentrated to a small volume and the dense residual oil was ground three times with 50 ml of anhydrous ethyl ether, discarding the ether solutions. The powdery white solid thus obtained was taken up with distilled water, filtering away the insoluble part, and freeze-dried. 1.170 g (70.1%) of a hygroscopic and analytically pure white solid were recovered.

The compound shows an excellent anti-hypertensive activity, with a reduction of 20% in the pressure value at 4 mg/Kg i.p. The anti-inflammatory effect also appears very good, with a 70% reduction of edema. The compound appears to increase the immune response.

The following compounds have been prepared in a similar manner:

(L)-Pyr-(L)-Ala-(L)-PhgOMe (L)-Pyr-(L)-Val-(L)-PhgOMe (L)-Pyr-(L)-Leu-(L)-PhgOMe

EXAMPLE 23

Synthesis and pharmacological activity of (L)-Pyr-Gly-(L)-Pme (compound 23)

A suspension of 1.830 g (5.00 mmoles) of the 2,4,5 trichlorophenol ester of (L)-Pyr-GlyOH acid (ester prepared according to Morley's method from the (L)-Pyr-GlyOH free acid [Novabiochem]) in 60 ml of dry methyl chloride ($CH_2Cl_2$) was brought under stirring and in an argon atmosphere to the temperature of an ice and salt bath. On stabilization of the temperature, a pre-cooled solution of 0.910 mg (5.51 mmoles) of (L)-Pme (prepared by partition between 5% $NaHCO_3$ and $CH_2Cl_2$, with the organic phase left to dry, after partition, for 12 hours on anhydrous $Na_2SO_4$, from the corresponding hydrochloride, (L)-Pme.HCl [Fluka]) in 40 ml of $CH_2Cl_2$. The temperature of the bath was kept under control for approximately one hour and then, leaving the temperature free to rise to room temperature, the mixture was left under stirring for a further 24 hours. The reaction mixture was then concentrated to a small volume and the dense residual oil was ground three times with 50 ml of anhydrous ethyl ether, discarding the ether solutions. The powdery white solid thus obtained was taken up with distilled water, filtering away the insoluble part, and freeze-dried. 1.250 g (74.9%) of a hygroscopic and analytically pure white solid were recovered.

The compound shows a good anti-hypertensive activity at 8 mg/Kg i.p. The compound also has an excellent analgesic effect (reduction of 80% in the Writhing test) and a good immuno-stimulating effect.

The following compounds have been prepared in a similar manner:

(L)-Pyr-(L)-Ala-(L)-Pme (L)-Pyr-(L)-Leu-(L)-Pme (L)-Pyr-(L)-Val-(L)-Pme (L)-Pyr-(L)-Ala-(L)-Pho (L)-Pyr-(L)-Leu-(L)-Pho (L)-Pyr-(L)-Val-(L)-Pho (L)-Pyr-Gly-(L)-Pho

EXAMPLE 24

Synthesis and pharmacological activity of (L)-Pyr-Gly-(L)-CypOMe (compound 24)

A suspension of 1.830 g (5.00 mmoles) of the 2,4,5 trichlorophenol ester of (L)-Pyr-GlyOH acid (ester prepared according to Morley's method from the (L)-Pyr-GlyOH free acid [Novabiochem]) in 60 ml of dry methyl chloride ($CH_2Cl_2$) was brought under stirring and in an argon atmosphere to the temperature of an ice and salt bath. On stabilization of the temperature, a pre-cooled solution of 1.050 mg (5.49 mmoles) of (L)-CypOMe (prepared by partition between 5% $NaHCO_3$ and $CH_2Cl_2$, with the organic phase left to dry, after partition, for 12 hours on anhydrous $Na_2SO_4$, from the corresponding hydrochloride, prepared as previously described for Z-Pro-Ala-CypOMe)

in 40 ml of $CH_2Cl_2$. The temperature of the bath was kept under control for approximately one hour and then, leaving the temperature free to rise to room temperature, the mixture was left under stirring for a further 24 hours. The reaction mixture was then concentrated to a small volume and the dense residual oil was ground three times with 50 ml of anhydrous n-hexane, discarding the ether solutions. The rubbery whitish solid thus obtained was taken up with a minimum quantity of $CH_2Cl_2$ and purified using flash-chromatography in a normal phase ($SiO_2$, eluant $CH_2Cl_2$). The chromatographic fractions of interest, after being recovered and concentrated to a small volume, were ground with dry petroleum ether (30/50), obtaining a white, slightly rubbery solid, which was left under vacuum on $P_2O_5$ for 24 hours. 1.240 g (68.9%) of an analytically pure white solid were recovered.

The compound shows a bland anti-hypertensive action and a moderate anti-inflammatory action.

The following compounds have been prepared in a similar manner:

(L)-Pyr-Gly-(1)-Me-(L)-CypOMe
(L)-Pyr-Gly-(6)-MeO-(L)-CypOMe
(L)-Pyr-Gly-(L)-Cpe
(L)-Pyr-(L)-Ala-(L)-CypOMe
(L)-Pyr-(L)-Leu-(L)-CypOMe
(L)-Pyr-(L)-Val-(L)-CypOMe
(L)-Pyr-(L)-Leu-(1)-Me-(L)-CypOMe
(L)-Pyr-(L)-Ala-(l)-Me-(L)-CypOMe
(L)-Pyr-(L)-Val-(l)-Me-(L)-CypOMe
(L)-Pyr-(L)-Leu-(6)-MeO-(L)-CypOMe
(L)-Pyr-Gly-(L)-Cpe
(L)-Pyr-Gly-(L)-OmtOMe
(L)-Pyr-(L)-Leu-(L)-OmtOMe
(L)-Pyr-(L)-Ala-(L)-OmtOMe
(L)-Pyr-(L)-Val-(L)-OmtOMe

EXAMPLE 25

Synthesis and pharmacological activity of (L)-Pyr-(L)-Leu-(S)-CytOMe (compound 25)

A suspension of 2.100 g (4.98 mmoles) of the 2,4,5 trichlorophenol ester of (L)-Pyr-(L)-LeuOH acid (ester prepared according to Morley's method from the (L)-Pyr-(L)-LeuOH free acid [Novabiochem]) in 60 ml of dry methyl chloride ($CH_2Cl_2$) was brought under stirring and in an argon atmosphere to the temperature of an ice and salt bath. On stabilization of the temperature, a pre-cooled solution of 1.260 g (5.46 mmoles) of (S)-CytOMe, prepared as previously described for Z-(L)-Pyr-(L)-Leu-(S)-CytOMe, in 40 ml of $CH_2Cl_2$. The temperature of the bath was kept under control for approximately one hour and then, leaving the temperature free to rise to room temperature, the mixture was left under stirring for a further 12 hours. The reaction mixture, concentrated to a small volume, was then added dropwise to approximately 200 ml of anhydrous ethyl ether ($Et_2O$), obtaining an abundant white precipitate which, after several hours at rest in a cold chamber, was vacuum filtered, discarding the ether solution. The white solid thus obtained was ground once again with anhydrous $Et_2O$ and left under vacuum on $P_2O_5$ for 24 hours. 1.880 g (79.8%) of an analytically pure white solid were recovered.

The compound has a bland anti-hypertensive effect, joined to a weak analgesic activity.

The following compounds have been prepared in a similar manner:

(L)-Pyr-(L)-Ala-(S)-CytOMe
(L)-Pyr-(L)-Val-(S)-CytOMe
(L)-Pyr-(L)-Leu-(1)-Me-(S)-CytOMe
(L)-Pyr-(L)-Ala-(1)-Me-(S)-CytOMe
(L)-Pyr-(L)-Leu-(9)-Me-(S)-CytOMe
(L)-Pyr-Gly-(l)-Me-(S)-CytoMe
(L)-Pyr-Gly-(S)-CytOMe

We claim:

1. Compounds of general formula A—B—C in which A is a monovalent radical of a ring molecule selected from the group consisting of:

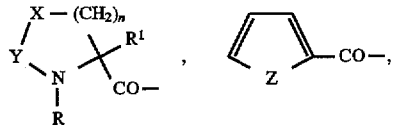
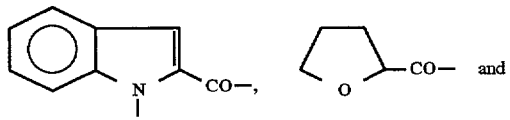
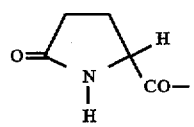

in which

X can be $CH_2$, S or CHOH n can be 0, 1, or 2

$R^1$ can be H or $CH_3$,

R can be H, $CH_3$, or a generic nitrogen blocking group as used in the synthesis of peptides selected from the group consisting of CBZ, BOC, Fmoc and acetyl Y can be $CH_2$, or CO Z can be NH, $NCH_3$, O or S;

B is a bivalent radical of an neutral (L)-α-amino acid, selected from the group consisting of glycine, leucine, alanine and valine; and C is the monovalent radical of a (L)-aromatic amino acid selected from the group consisting of MeCytOMe, MeCytOH, CytOMe, CytOH, CypOMe, TrpOMe, PhgOMe, wherein CBZ is carbobenzoxy, MeCytOMe is methyl-(1)-methyl-(S)-1,2,3,4-tetrahydro-9H-pyrido[3,4b]-indole-3-carboxylate, or MeCytOMe is methyl-(9)-methyl-(S)-1,2,3,4-tetrahydro-9H-pyrido[3,4-b]-indole-3-carboxylate, or MeCytOMe is methyl-(5)-methyl-(S)-1,2,3,4-tetrahydro-9H-pyrido[3,4-b]-indole-3-carboxylate, MeCytOH is the free acid form of MeCytOMe, CytOMe is methyl-(S)-1,2,3,4-tetrahydro-9H-pyrido [3,4-b]-indole-3-carboxylate, CytOH is the free acid form of CytOMe, CyoOMe is (L)-1,2,3,4-tetrahydro-3-isoquinoline methyl ester, TrpOMe is tryptophan methyl ester, PhgOMe is phenyl-glycine methyl ester and salts, esters and amides thereof, wherein the compound of formula A—B—C is not N-CBZ-Pro-Leu-CytOEt,
N-CBZ-Pro-Ala-PhgOMe
2-Fur-Leu-TrPOMe,
2-Tiof-Leu-TrpOMe,
2-Pyrrolyl-Leu-TrpOMe, N-Me-Pro-Ala-CytOMe,
N-CBZ-Pip-Leu-TrpOME,
Pyr-Leu-Cyt, or
2-Fur-Leu-CytOMe,
with the proviso that when A is

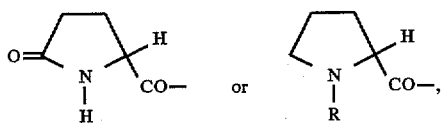

in which R has the meaning previously indicated, with the exclusion of CH₃, then C cannot be either a residue of trytophan, or of phenylalanine.

2. A method for the treatment of hypertension which comprises administering an effective amount of a compound according to claim 1 to a patient in need thereof.

3. A method for the treatment of pain which comprises administering an effective amount of a compound according to claim 1 to a patient in need thereof.

4. A method for modulating the immune response which comprises administering an effective amount of a compound according to claim 1 to a patient in need thereof.

5. A method for the treatment of inflammatory states which comprises administering an effective amount of a compound according to claim 1 to a patient in need thereof.

6. A method according to any one of claims 2–5 which comprises orally administering said compound.

7. A pharmaceutical composition comprising a pharmaceutically acceptable excipient and a pharmacologically active compound of the following general formula:

A—B—C in which A is a monovalent radical of a ring molecule selected from the group consisting of:

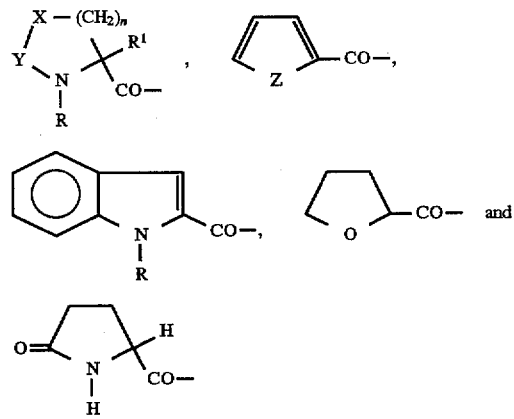

in which
X can be CH₂, S or CHOH
n can be 0, 1, or 2
R¹ can be H or CH₃
R can be H, CH₃, or a generic nitrogen blocking group as used in the synthesis of peptides selected from the group consisting of CBZ, BOC, Fmoc and acetyl
Y can be CH₂, or CO
Z can be NH, NCH₃, O or S;
B is a bivalent radical of an neutral (L)-α-amino acid, selected from the group consisting of glycine, leucine, alanine and valine; and C is the monovalent radical of a (L)-aromatic amino acid selected from the group consisting of MeCytOMe, MeCytOH, CytOMe, CytOH, CypOMe, TrpOMe, PhgOMe, wherein CBZ is carbobenzoxy, MeCytOMe is methyl-(1)-methyl-(S)-1,2,3,4-tetrahydro-9H-pyrido[3,4-b]-indole-3-carboxylate, or MeCytOMe is methyl-(9)-methyl-(S)-1,2,3,4-tetrahydro-9H-pyrido[3,4-b]-indole-3-carboxylate, or MeCytOMe is methyl-(S)-methyl-(S)-1,2,3,4-tetrahydro-9H-pyrido[3,4-b]-indole-3-carboxylate, MeCytOH is the free acid form of MeCytOMe, CytOMe is methyl-(S)-1,2,3,4-tetrahydro-9H-pyrido[3,4-b]-indole-3-carboxylate, CytOH is the free acid form of CytOMe, CypOMe is (L)-1,2,3,4-tetrahydro-3-isoquinoline methyl ester, TrpOMe is tryptophan methyl ester, PhgOMe is phenyl-glycine methyl ester and salts, esters and amides thereof, wherein the compound of formula A-B-C is not N-CBZ-Pro-Leu-CytOEt,
N-CBZ-Pro-Ala-PhgOMe
2-Fur-Leu-TrpOMe,
2-Tiof-Leu-TrpOMe,
2-Pyrrolyl-Leu-TrpOMe,
N-Me-Pro-Ala-CytOMe,
N-CBZ-Pip-Leu-TrpOMe,
Pyr-Leu-Cyt, or
2-Fur-Leu-CytOMe,
with the proviso that when A is

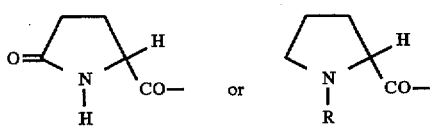

in which R has the meaning previously indicated, with the exclusion of CH₃, then C cannot be either a residue of trytophan, or of phenylalanine.

8. A pharmaceutical composition according to claim 7, wherein said pharmaceutically acceptable excipient is selected from the group consisting of diluents, fillers, binders, moistening agents, reticulating agents, adsorption agents, agents for delaying solution and agents for accelerating absorption.

9. A pharmaceutical composition according to claim 7 wherein said pharmacologically active compound is selected from the group consisting of:

2-Fur-(L)-Leu-(L)-CytOMe,
2-Fur-(L)-Leu-(L)-MeCytOH, and
2-Fur-(L)-Leu-(L)-TrpOMe.

10. A pharmaceutical composition according to claim 7 wherein said pharmacologically active compound is selected from the group consisting of:

N-Me-(L)-ProLeu-(S)-TrpOMe,
N-Me-(L)-ProLeu-(S)-CytOMe, and
N-Me-(L)-ProLeu-(S)-MeCytOH.

11. A pharmaceutical composition according to claim 7 wherein said pharmacologically active compound is selected from the group consisting of:

(L)-Pyr-(L)-Leu-(S)-CypOMe,
(L)-Pyr-(L)-Leu-(S)-CytOMe, and
(L)-Pyr-(L)-Leu-(S)-MeCytOMe.

12. A pharmaceutical composition according to claim 7 wherein said pharmacologically active compound is selected from the group consisting of:

Tfc-(L)-Leu-(S)-Me-CytOH, and

Tfc-(L)-Leu-(S)-CytOH.

13. A pharmaceutical composition according to claim 7 wherein said pharmacologically active compound is selected from the group consisting of:

2-Tiof-(L)-Leu-(L)-MeCytOH, and

2-Tiof-(L)-Leu-(L)-CytOMe.

14. A pharmaceutical composition according to claim 7 wherein said pharmacologically active compound is selected from the group consisting of:

Z-(L)-Pro-(L)-Ala-(S)-CypOMe,

Z-(L)-Pro-(L)-Ala-(S)-CytOH,

Z-(L)-Pro-(L)-Ala-(S)-CytoMe, and

Z-(L)-Pro-(L)-Ala-(S)-MeCytOMe.

15. A pharmaceutical composition according to claim 7 wherein said pharmacologically active compound is selected from the group consisting of:

Z-(L)-Pro-(L)-Leu-(S)-CytOMe,

Z-(L)-Pro-(L)-Leu-(S)-PhgOMe, and

Z-(L)-Pro-(L)-Leu-(S)-MeCytOMe.

16. A pharmaceutical composition according to claim 7 wherein said pharmacologically active compound is selected from the group consisting of:

Z-(L)-Pyr-(L)-Leu-(S)-CytOMe.

17. A pharmaceutical composition according to claim 7 wherein said pharmacologically active compound is selected from the group consisting of:

Boc-(L)-(cis,trans)-(L)-Hyp-(L)-Leu-(S)-CytOH,

Boc-(L)-Pro-(L)-Leu-(S)-CytOH, and (L)-Hyp-(L)-Leu-(S)-CytOH.

18. A pharmaceutical composition according to claim 7 wherein said pharmacologically active compound is selected from the group consisting of:

2-Indolyl-(L)-Ala-(S)-CytOMe,

N-Me-(L)-Pro-(L)-Ala-(S)-CytOMe, (L)-Pip-(L)-Ala-(S)-CytOMe, and (L)-Pyr-(L)-Ala-(S)-CytOMe.

19. A pharmaceutical composition according to claim 7 wherein said pharmacologically active compound is selected from the group consisting of:

1-Me-2-Pyrrolyl-(L)-Leu-(L)-TrpOMe, and

Z-(L)-Pip-(L)-Leu-(L)-TrpOMe.

20. A pharmaceutical composition according to claim 7 wherein said pharmacologically active compound is (L)-Pyr-Gly-CytOMe.

21. A pharmaceutical composition according to claim 7 wherein said pharmacologically active compound is 2-Pyrrolyl-Gly-PhgOMe.

22. A pharmaceutical composition according to claim 7 wherein said pharmacologically active compound is Z-(L)-Pro-(L)-Val-CytOMe.

* * * * *